United States Patent
Madhuranthakam et al.

(10) Patent No.: US 11,169,237 B2
(45) Date of Patent: Nov. 9, 2021

(54) PHASE SENSITIVE MAGNETIC RESONANCE ANGIOGRAPHY

(71) Applicant: BOARD OF REGENTS, THE UNIVERSITY OF TEXAS SYSTEM, Austin, TX (US)

(72) Inventors: Ananth J. Madhuranthakam, Coppell, TX (US); Xinzeng Wang, Houston, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 766 days.

(21) Appl. No.: 15/762,794

(22) PCT Filed: Oct. 5, 2016

(86) PCT No.: PCT/US2016/055523
§ 371 (c)(1),
(2) Date: Mar. 23, 2018

(87) PCT Pub. No.: WO2017/062470
PCT Pub. Date: Apr. 13, 2017

(65) Prior Publication Data
US 2018/0284209 A1 Oct. 4, 2018

Related U.S. Application Data

(60) Provisional application No. 62/237,285, filed on Oct. 5, 2015.

(51) Int. Cl.
*G01R 33/563* (2006.01)
*A61B 5/026* (2006.01)
(Continued)

(52) U.S. Cl.
CPC .... *G01R 33/56316* (2013.01); *A61B 5/02007* (2013.01); *A61B 5/0263* (2013.01);
(Continued)

(58) Field of Classification Search
None
See application file for complete search history.

(56) References Cited

U.S. PATENT DOCUMENTS 6,192,264 B1 2/2001 Foo et al.
6,246,897 B1 6/2001 Foo et al.
(Continued)

FOREIGN PATENT DOCUMENTS

JP 2000-175885 A 6/2000
JP 2008-125891 A 6/2008
(Continued)

OTHER PUBLICATIONS

Fan, et al. "3D noncontrast MR angiography of the distal lower extremities using flow-sensitive dephasing (FSD)-prepared balanced SSFP" Magn Reson Med, Dec. 2009; 62(6): 1523-1532.
(Continued)

*Primary Examiner* — Jonathan Cwern
(74) *Attorney, Agent, or Firm* — Edwin S. Flores; Daniel J. Chalker; Chalker Flores, LLP

(57) ABSTRACT

The present invention includes a computerized method of detecting fluid flow in a vessel, the method comprising: obtaining at least one non-contrast enhanced magnetic resonance image from a magnetic resonance imager; performing a phase sensitive reconstruction of the at least one non-contrast enhanced magnetic resonance image using a processor; combining the phase sensitive reconstruction with a velocity selective preparation of the non-contrast enhanced magnetic resonance image, to determine using the processor, in a single acquisition, at least one of: a flow direction of a
(Continued)

fluid in the vessel, a reduction or elimination of a background signal, body fat, water/fat separation, or differentiation of a fast moving flow signal from a slow moving flow signal in an opposite direction with suppression of the background signal; and storing or displaying at least one of flow direction or flow strength of the fluid flow in the vessel obtained from the single acquisition.

23 Claims, 12 Drawing Sheets

(51) Int. Cl.
    *A61B 5/055*     (2006.01)
    *A61B 5/02*     (2006.01)
    *G01R 33/561*     (2006.01)

(52) U.S. Cl.
    CPC .......... *A61B 5/055* (2013.01); *G01R 33/5614* (2013.01); *G01R 33/5616* (2013.01); *G01R 33/5635* (2013.01); *A61B 2576/02* (2013.01)

(56) References Cited

U.S. PATENT DOCUMENTS

| | | | |
|---|---|---|---|
| 8,410,779 | B2 | 4/2013 | Deimling et al. |
| 8,744,551 | B2 | 6/2014 | Koktzoglou et al. |
| 8,855,743 | B2 | 10/2014 | Hoshino et al. |
| 9,036,320 | B1 | 5/2015 | Elberbaum |
| 2008/0119721 | A1 | 5/2008 | Kimura et al. |
| 2012/0283547 | A1* | 11/2012 | Wong ............... A61B 5/055 600/410 |
| 2015/0305645 | A1* | 10/2015 | Ouyang ........... G01R 33/56366 600/419 |

FOREIGN PATENT DOCUMENTS

| | | |
|---|---|---|
| WO | 2003/008989 A1 | 1/2003 |
| WO | 2011/132593 A1 | 10/2011 |
| WO | 2017/062470 A1 | 4/2017 |

OTHER PUBLICATIONS

Korean Intellectual Property Office, International Search Report and Written Opinion for PCT/US2016/055523, dated Jan. 10, 2017, 11 pp.

Kellman, et al. "Phase-sensitive inversion recovery for detecting myocardial infarction using gadolinium-delayed hyperenhancement" Magn Reson Med, Feb. 2002; 47(2):372-383.

Miyazaki, et al. "Nonenhanced MR angiography" Radiology, Jul. 2008; 248(1):20-43.

\* cited by examiner

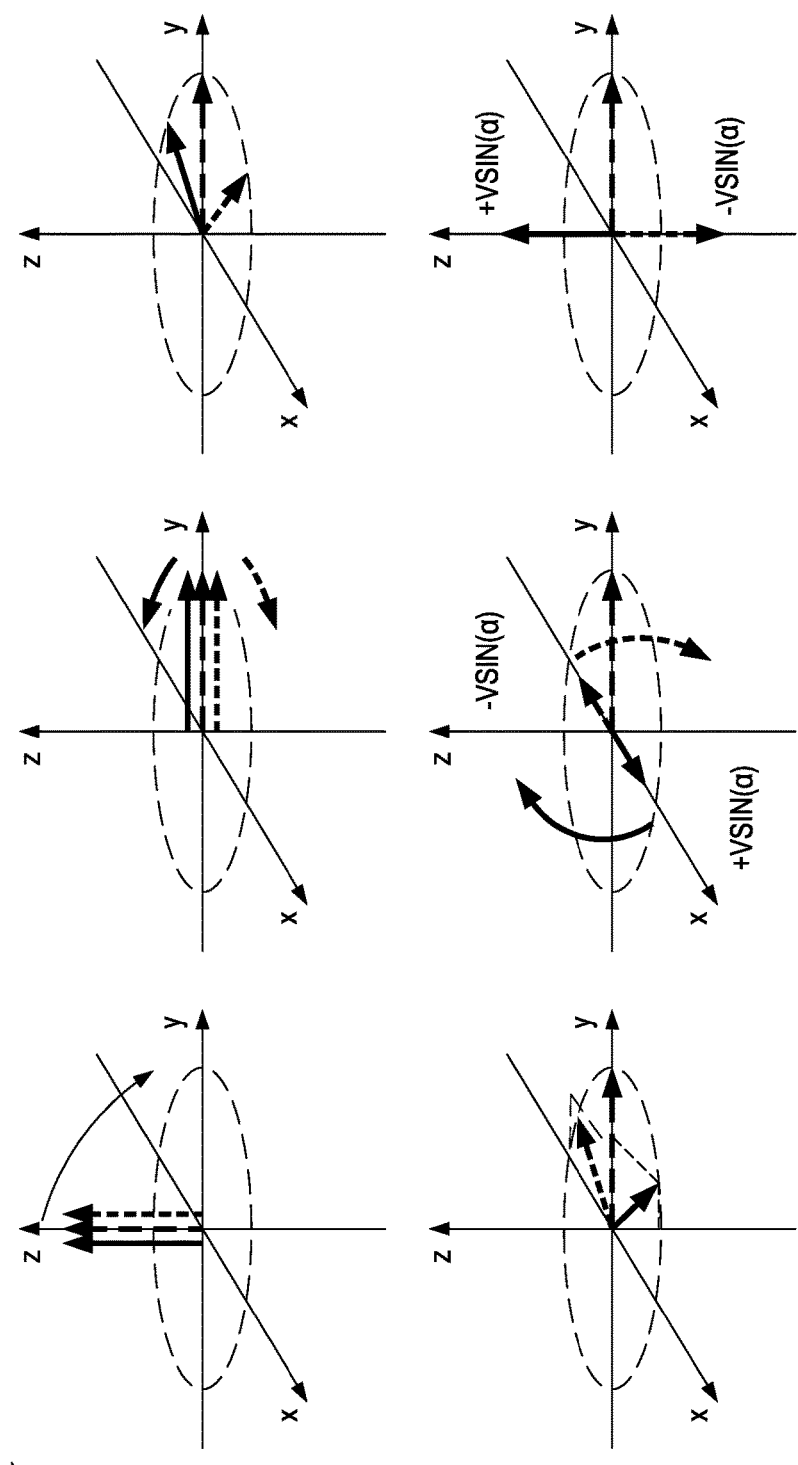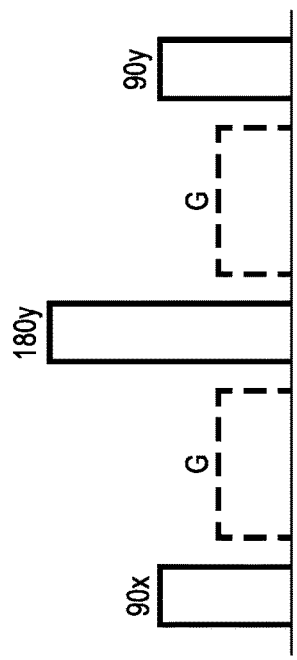
FIG. 1A
FIG. 1B

PHASE SENSITIVE MAGNETIC RESONANCE ANGIOGRAPHY

CROSS-REFERENCE TO RELATED APPLICATIONS

This application is a National Stage of International Application No. PCT/US2016/055523, filed Oct. 5, 2016, which claims the benefit of U.S. Provisional Application No. 62/237,285, filed Oct. 5, 2015. The contents of each of which are incorporated by reference in their entirety.

TECHNICAL FIELD OF THE INVENTION

The present invention relates in general to the field of magnetic resonance angiography, and more particularly, to a novel phase sensitive method of magnetic resonance angiography.

STATEMENT OF FEDERALL FUNDED RESEARCH

Not applicable.

BACKGROUND OF THE INVENTION

Without limiting the scope of the invention, its background is described in connection with magnetic resonance imaging.

One such invention is taught in U.S. Pat. No. 8,744,551, issued to Koktzoglou, et al., is entitled "Method for non-contrast enhanced magnetic resonance angiography." Briefly, these inventors are said to teach a method for non-contrast enhanced magnetic resonance angiography (MRA) of a three-dimensional (3D) volume of a subject having a vascular structure extending through the 3D volume and having flowing spins passing through vascular structure. The method includes applying at least one radiofrequency (RF) pulse to a first slice to label the flowing spins passing into a second slice located within the 3D volume adjacent to the first slice and acquiring imaging data from the second slice using a two-dimensional (2D) pulse sequence and sampling k-space using a non-Cartesian sampling pattern. The acquisition of the imaging data is repeated to acquire a series of second slices located across the 3D volume to acquire respective sets of imaging data spanning the 3D volume. The sets of imaging data are reconstructed into a time-series of image frames depicting the flowing spins passing through the vascular structure.

Another method is taught in U.S. Pat. No. 8,410,779, issued to Deimling, et al., entitled "Contrast agent-free MR angiography with SSFP sequences." Briefly, these inventors are said to teach a method of generating an MR angiography image of an examination region of a subject without the use of contrast agent, in which a first MR image of the examination region is acquired with a first imaging sequence in which a gradient-induced phase development for unmoved and moved spins is essentially completely rephased at the end of a repetition interval TR, and a second MR image of the examination region is also acquired with a second imaging sequence in which the gradient-induced phase development for unmoved spins is likewise essentially completely rephased at the end of the repetition interval TR and a rest phase for moved spins remains at the end of the repetition interval TR, in which the second MR image is subtracted from the first MR image to generate the MR angiography image.

Yet another method is taught in United States Patent Publication No. 2013/0303885, filed by Hoshino, et al., entitled "Non-contrast magnetic resonance perfusion imaging." Briefly, these applicants are said to teach a magnetic resonance imaging (MRI) system that acquires MRI data within one patient breath-hold sufficient to generate (a) at least one tag-off first type non-contrast cardiac perfusion image using a data acquisition sub-sequence including a non-selective IR (inversion recovery) pulse and (b) at least one tag-on second type non-contrast cardiac perfusion image using a data acquisition sub-sequence including a non-selective IR pulse and a spatially selective IR pulse, in which a set of registered tag-on and tag-off images are differentially combined to produce an accurate cardiac perfusion image.

SUMMARY OF THE INVENTION

In one embodiment, the present invention includes a computerized method of detecting fluid flow in a vessel, the method comprising: obtaining at least one non-contrast enhanced magnetic resonance image from a magnetic resonance imager; performing a phase sensitive reconstruction of the at least one non-contrast enhanced magnetic resonance image using a processor; combining the phase sensitive reconstruction with a velocity selective preparation of the non-contrast enhanced magnetic resonance image, to determine using the processor, in a single acquisition, at least one of: a flow direction of a fluid in the vessel, a reduction or elimination of a background signal, body fat, water/fat separation, or differentiation of a fast moving flow signal from a slow moving flow signal in an opposite direction with suppression of the background signal; and storing or displaying at least one of flow direction or flow strength of the fluid flow in the vessel obtained from the single acquisition. In one aspect, the method further comprises the step of velocity selective preparation using a magnetization preparation from one or more $90°_x$-$180°_y$-$90°_y$ radio frequency (RF) pulse trains. In another aspect, the method further comprises the step of velocity selective preparation using a magnetization preparation using a $90°_x$-$180°_y$-$90°_y$ radio frequency (RF) pulse train with one or more velocity encoding gradients applied between one or more RF pulses of the RF pulse train. In another aspect, the method further comprises the step of velocity selective preparation using a process implemented in a 2D balanced steady state free precession (bSSFP) acquisition. In another aspect, the method further comprises the step of obtaining an additional image using $90°_x$-$180°_y$-$90°_{-x}$ and without a velocity selective preparation gradient, wherein the additional image is used to determine a phase for the phase sensitive reconstruction. In another aspect, the method further comprises the step of using a B1-insensitive rotation (BIR-4) pulse with flip angle (FA) 90° with velocity selective gradients to acquire the velocity sensitive image with high efficiency and another image using BIR-4 pulse with FA 0° and without velocity selective gradients to determine phase for phase sensitive reconstruction. In another aspect, the method further comprises the step of obtaining an image of a blood vessel of an animal or a human. In another aspect, the method further comprises the step of detecting the moving flow signal in one direction from an arterial flow and the moving flow signal in the opposite direction from a venous flow. In another aspect, the method further comprises the step of acquiring a reference image using $90°_x$-$180°_y$-$90°_{-x}$ or BIR-4 with flip angle (FA) 0°, and a magnitude image is acquired with velocity selective preparation, and using the reference image and the magnitude image to obtain a phase sensitive image that shows flow direction. In another aspect, the method further comprises the step of obtaining the image is defined further as comprising a data acquisition method selected from at least one of: balanced steady state free precession (bSSFP), fast or turbo spin echo (FSE/TSE), or gradient echo. In another aspect, the method further comprises the step of obtaining a bSSFP image is defined further as using at least one imaging parameter selected from: TR/TE=3.1/1.56 ms, matrix size=220×216, voxel size=1.1×1.1×4 mm³, or centric phase encoding.

Yet another embodiment of the present invention includes a computerized method of performing an angiography that separates arterial from venous flow comprising: providing a magnetic resonance imager; obtaining at least one non-contrast enhanced magnetic resonance image of a blood vessel with the magnetic resonance imager; performing a phase sensitive reconstruction of the at least one non-contrast enhanced magnetic resonance image of the blood vessel using a processor; combining the phase sensitive reconstruction with a velocity selective preparation of the non-contrast enhanced magnetic resonance image of the blood vessel, to determine using the processor, in a single acquisition, at least one of: a flow direction of blood in the blood vessel, a reduction or elimination of a background signal caused by venous flow, body fat, water/fat separation, or differentiation of a fast moving arterial blood flow signal from a slow moving venous blood flow signal in an opposite direction with suppression of the background signal; and storing or displaying at least one of flow direction or flow strength of the fluid flow in the vessel obtained from the single acquisition. In one aspect, the method further comprises the step of velocity selective preparation using a magnetization preparation from one or more $90°_x$-$180°_y$-$90°_y$ radio frequency (RF) pulse trains. In another aspect, the method further comprises the step of velocity selective preparation using a magnetization preparation using a $90°_x$-$180°_y$-$90°_y$ radio frequency (RF) pulse train with one or more velocity encoding gradients applied between one or more RF pulses of the RF pulse train. In another aspect, the method further comprises the step of velocity selective preparation using a process implemented in a 2D balanced steady state free precession (bSSFP) acquisition. In another aspect, the method further comprises the step of obtaining an additional image using $90°_x$-$180°_y$-$90°_{-x}$ and without a velocity selective preparation gradient, wherein the additional image is used to determine a phase for the phase sensitive reconstruction. In another aspect, the method further comprising the step of using a B1-insensitive rotation (BIR-4) pulse with flip angle (FA) 90° with velocity selective gradients to acquire the velocity sensitive image with high efficiency and another image using a BIR-4 pulse with FA 0° and without velocity selective gradients to determine phase for phase sensitive reconstruction. In another aspect, the method further comprises the step of obtaining an image of a blood vessel of an animal or a human. In another aspect, the method further comprises the step of detecting the fast moving flow signal in a first direction from an arterial flow and the slow moving flow signal in the opposite direction from a venous flow. In another aspect, the method further comprises the step of acquiring a reference image using BIR-4 with flip angle (FA) 0°, and a magnitude image is acquired with velocity selective preparation, and using the reference image and the magnitude image to obtain a phase sensitive image that shows flow direction. In another aspect, the method further comprises the step of obtaining the image is defined further as comprising a data acquisition method selected from at least one of: balanced steady state free precession (bSSFP), fast or turbo spin echo (FSE/TSE), or gradient echo. In another aspect, the method further comprises the step of obtaining a bSSFP image is defined further as using at least one imaging parameter selected from: TR/TE=3.1/1.56 ms, matrix size=220×216, voxel size=1.1×1.1×4 mm³' or centric phase encoding.

Yet another embodiment of the present invention includes a magnetic resonance imaging apparatus improved by a computerized method comprising: obtaining at least one non-contrast enhanced magnetic resonance image from a magnetic resonance imager; performing a phase sensitive reconstruction of the at least one non-contrast enhanced magnetic resonance image using a processor; combining the phase sensitive reconstruction with a velocity selective preparation of the non-contrast enhanced magnetic resonance image with the processor to determine at least one of a flow direction of a fluid in the vessel, a reduction or elimination of a background signal, or differentiation of a fast moving arterial blood flow signal from a slow moving venous blood flow signal in an opposite direction with suppression of the background signal in a single acquisition; and storing or displaying at least one of flow direction or flow strength of the fluid flow in the vessel obtained from the single acquisition. In one aspect, the method further comprises the step of velocity selective preparation using a magnetization preparation using a $90°_x$-$180°_y$-$90°_y$ radio frequency (RF) pulse train with one or more velocity encoding gradients applied between one or more RF pulses of the RF pulse train.

Yet another embodiment of the present invention includes a non-transitory computer readable medium for determining at least one of flow direction or flow strength of a fluid flow in a blood vessel, comprising instructions stored thereon, that when executed by a computer having a communications interface, one or more databases and one or more processors communicably coupled to the interface and one or more databases, perform the steps comprising: obtaining at least one non-contrast enhanced magnetic resonance image from a magnetic resonance imager; performing a phase sensitive reconstruction of the at least one non-contrast enhanced magnetic resonance image using a processor; combining the phase sensitive reconstruction with a velocity selective preparation of the non-contrast enhanced magnetic resonance image with the processor to determine at least one of a flow direction of a fluid in the vessel, a reduction or elimination of a background signal, or differentiation of a fast moving arterial blood flow signal from a slow moving venous blood flow signal in an opposite direction with suppression of the background signal in a single acquisition; and storing on the computer or in the one or more databases or displaying on the communications interface, at least one of the flow direction or the flow strength of the fluid flow in the blood vessel obtained from the single acquisition.

BRIEF DESCRIPTION OF THE DRAWINGS

For a more complete understanding of the features and advantages of the present invention, reference is now made to the detailed description of the invention along with the accompanying figures and in which:

FIG. 1A shows a schematic of the magnetization evolution during velocity selective preparation (VSP) (red arrow represents a static spin; blue and green arrows represent moving spins in opposite directions), a represents the phase accumulation.

FIG. 1B is a graph of the pulse sequence that shows the basic velocity selective preparation (VSP) pulse of 90x-180y-90y and velocity encoding gradient, G.

FIG. 3A was acquired with BIR-4 FA 0° without velocity encoding gradient and FIG. 3B was acquired with VSP using BIR-4 based 90° with velocity encoding gradients (FIG. 3B).

FIG. 4B shows a color depiction with arterial signal (red) can be differentiated from venous signal (blue).

FIG. 5A is a reference image acquired using FA 0° BIR-4;

FIG. 5B is a magnitude image acquired with VSP; FIG. 5C is a phase sensitive image depicting flow direction.

FIG. 6A a positive gradient, FIG. 6B a negative gradient, FIG. 6C a subtracted image between FIGS. 6A and 6B. FIG. 6D is a reference image used for phase sensitive reconstruction.

DETAILED DESCRIPTION OF THE INVENTION

Figure 1C:
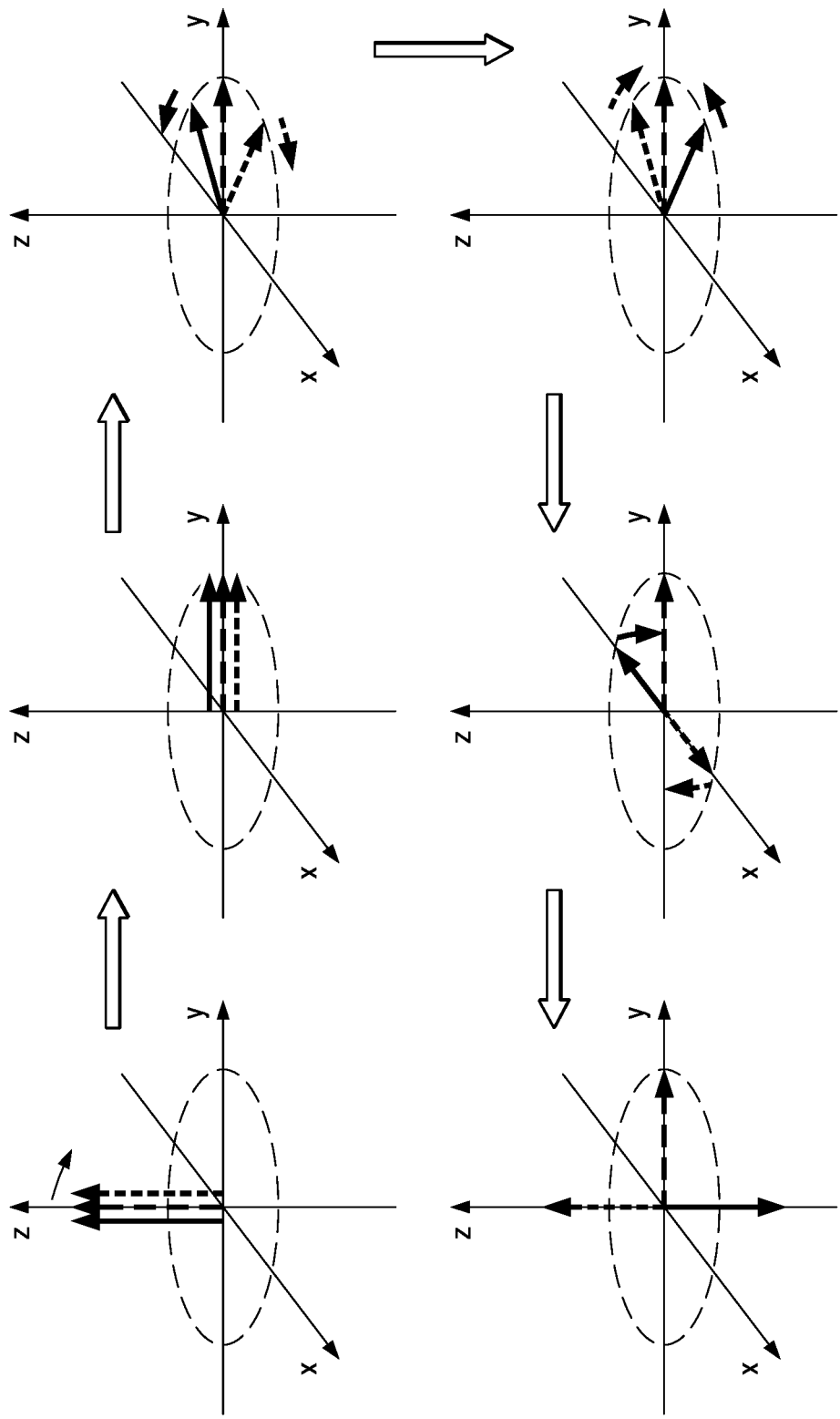
FIG. 1C shows one method of using the spin behavior with the VSP beginning at the top left and working across the top graphs following the arrows.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Magnetic Resonance Angiography (MRA) is increasingly used in the clinical practice for diagnosis and evaluation of various vascular malformations. Majority of the MRA techniques are performed with the administration of an exogenous contrast agent. However, gadolinium based exogenous contrast agents are contraindicated in a subset of populations with impaired renal function (1). In recent years, there has been renewed interest in the non-contrast enhanced (NCE) MRA techniques (2). Among various approaches, motion sensitized driven equilibrium (MSDE) based NCE-MRA has shown considerable promise (3). These approaches include multiple acquisitions with different MSDE preparations, which are then subtracted to achieve the final angiogram. The empirical settings of the MSDE gradients used with these approaches, combined with possible patient motion between the acquisitions, often lead to incomplete background signal suppression and venous signal contamination. An alternative approach using velocity selective preparation (VSP) was previously proposed (4), however, the background signal was not completely eliminated in a single acquisition and the velocity encoding used with this approach lead to venous signal contamination.

In this disclosure, the present inventors provide a method for using an efficient 90-degree MSDE preparation using an adiabatic BIR-4, which completely eliminates the background signal, and combine this with phase sensitive reconstruction (5) to determine the flow direction and potentially differentiate arterial and venous signal with background signal suppression in a single acquisition.

The present invention includes one or more of the following advantages: (1) use of a robust MSDE preparation using an adiabatic BIR-4 pulse with 90-degree flip angle, that essentially generates close to zero background signal; (2) use of phase sensitive acquisition and reconstruction to determine the flow direction; (3) the determination of flow direction allows separation of arteries and veins providing diagnostic information for both arteriogram and venogram; and/or (4) the estimation of flow direction overcomes the requirement for the optimization of the MSDE gradients.

Yet another advantage of the present invention is that it solves the problem of the generation of MR arteriogram and venogram from a single acquisition with directional flow and minimized background signal without the administration of exogenous contrast agent and without the optimization of the motion sensitizing gradients.

The present invention differs from existing art for at least the following reasons:
(1) The majority of the existing MSDE techniques uses so-called 0-degree MSDE preparation. With this approach, typically two images are acquired—one with appropriate motion sensitizing gradients to achieve an arterial black-blood signal and the other with appropriate motion sensitizing gradients to achieve an arterial bright-blood signal (3).

In both of these images, the background signal and the venous signal appear bright, which when subtracted cancels out leaving the arterial signal. Compared to this prior art, our approach uses a 90-degree MSDE preparation to selectively excite signals from the moving spins, while minimizing the background signal.

(2) An earlier proposed approach, called velocity selective preparation (VSP), where the 90-degree MSDE preparation was used (4), however, with their approach, the background signal was not eliminated completely, which forced them to acquire two images with different 90-degree MSDE preparation (using opposite gradients), which when subtracted suppressed the background signal. Compared to this prior art, our approach uses a more efficient 90-degree MSDE preparation using an adiabatic BIR-4 pulse that essentially achieves complete background signal suppression.

(3) As with the VSP approach described in (2) above, although the background signal was suppressed after subtraction, the MSDE gradients need to be adjusted such that only arterial signal is enhanced, while the venous signal is minimized due to its slower flow. However, there is a potential for venous contamination with this approach if the arterial flow is also decreased in pathology. Moreover, the venous signal with this approach is suppressed without providing any additional diagnostic information.

Compared to the prior art, the approach of the present invention uses a phase sensitive acquisition and reconstruction such that flow direction is estimated, allowing arterial and venous separation, providing diagnostic information for both arteries and veins in a single acquisition.

Example 1

The present invention is a phase sensitive reconstruction combined with velocity selective preparation (VSP) that is used in a method to determine the flow direction and can potentially differentiate arterial and venous signals with background signal suppression in a single acquisition.

Velocity selective preparation (VSP) uses magnetization preparation using a $90°_x$-$180°_y$-$90°_y$ radio frequency (RF) pulse train with velocity encoding gradients applied between the RF pulses. FIG. 1A shows a schematic of the spin behavior experiencing the VSP. The static spins (red arrow) accumulate the same amount of phase between the $90°_x$-$180°_y$ and $180°_y$-$90°_y$ and are aligned along the initial orientation (i.e. y-direction). However, the moving spins (blue and green arrows) accumulate phase depending upon their direction and velocity, i.e., arteries and veins accumulate different phase in opposite directions. Hence, at the end of the VSP, the static spins are oriented along the transverse plane while the moving spins in the opposite direction are oriented along the longitudinal direction (+z and −z). Spoiler gradients applied immediately after the VSP destroy the static signal while preserving the signal from the moving spins. A phase sensitive acquisition that follows immediately can measure the signals and the directions of the moving spins.

FIG. 1B is a graph that shows the basic MSDE pulse consisting 90x-180y-90y and velocity encoding gradient, G. FIG. 1C shows one method of using the spin behavior with the VSP beginning at the top left and working across the top graphs following the arrows. With selected gradient, spins (green and blue) moving in opposite directions were tipped back to z-axis while static spin (red) was left in x,y-plane at the end of 90y-RF.

Figure 2A:
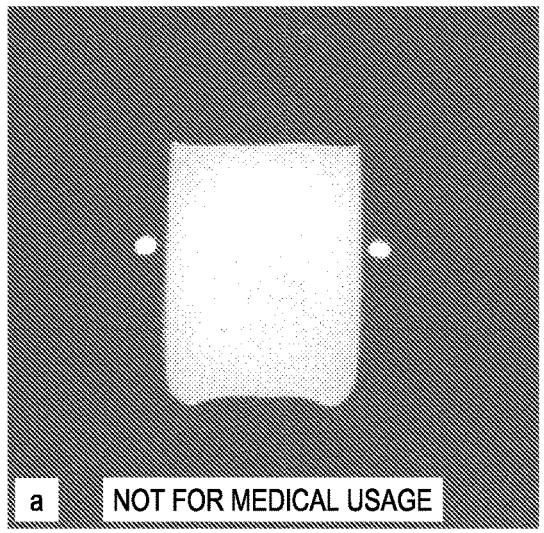
FIGS. 2A and 2B show a static phantom set up with the cylinder in the middle containing agarose gel and the two tubes next to it, carrying static water without any flow, acquired using BIR-4 FA 0° without velocity encoding gradients (FIG. 2A) and with VSP using BIR-4 FA 90° with velocity encoding gradients (FIG. 2B).
Figure 2B:
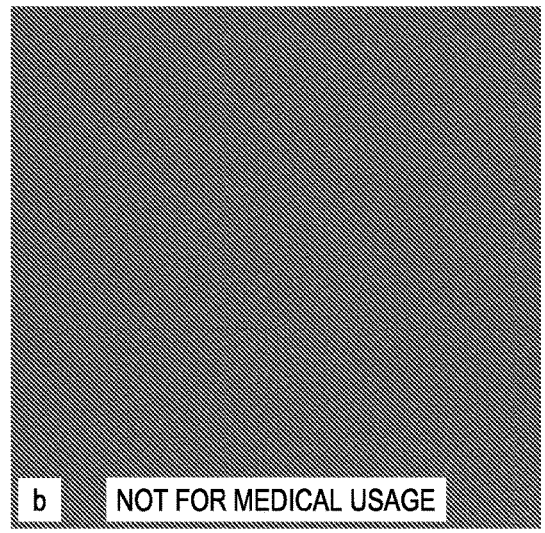

FIGS. 2A and 2B show a static phantom set up with the cylinder in the middle containing agarose gel and the two tubes next to it, carrying static water. For this experiment, the flow was turned off. The image in FIG. 2A was acquired with a standard 0-degree MSDE using the BIR-4 pulse. The image in FIG. 2B was acquired with a BIR-4 based 90-degree MSDE, essentially suppressing the static phantom signal completely to the background noise level.

Figure 3A:
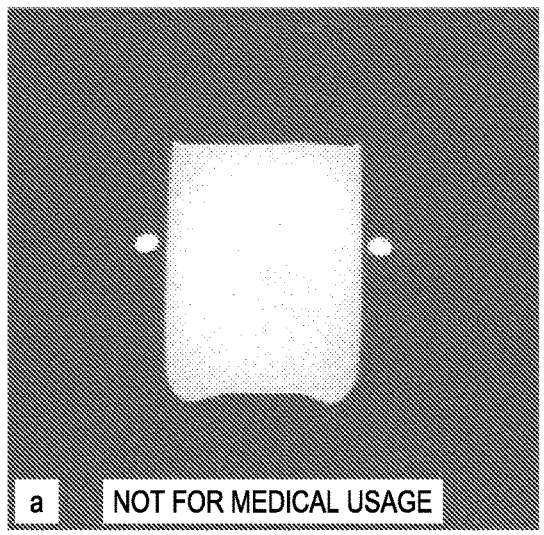
FIGS. 3A and 3B show the same phantom as above (FIGS. 2A and 2B, respectively), but with the flow turned on to mimic the arterial flow (towards the phantom) and the venous flow (away from the phantom).
Figure 3B:
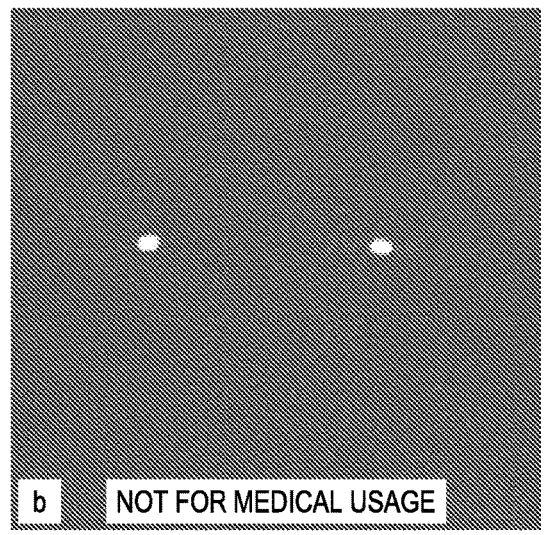

FIGS. 3A and 3B show the same phantom as above (FIGS. 2A and 2B, respectively), but with the flow turned on to mimic the arterial flow (towards the phantom) and the venous flow (away from the phantom). The image in FIG. 3A was acquired with a standard 0-degree MSDE using the BIR-4 pulse showing similar result to FIG. 2A, without the flow. The image in FIG. 3B was acquired with a BIR-4 based 90-degree MSDE, preserving the signal in the flow phantom, but suppressing the static phantom signal completely to the background noise level.

Figure 4A:
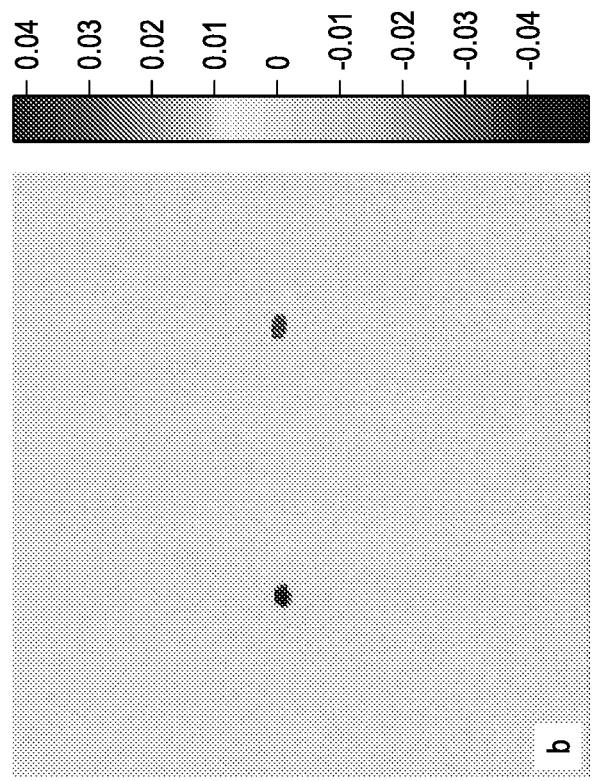
FIGS. 4A and 4B show the present invention using the phase sensitive reconstruction, the direction of the flow (see FIG. 1) can be determined from FIG. 3B. The phase sensitive reconstructed image is shown in (FIG. 4A) with the bright signal showing the signal intensity towards the phantom and the dark signal showing the signal away from the phantom, with completely suppressed background signal showing close to zero-signal.
Figure 4B:
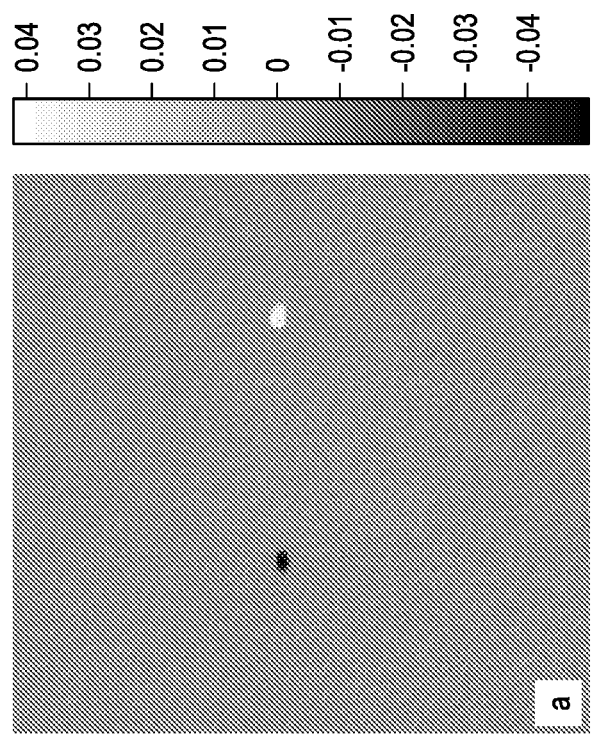

FIGS. 4A and 4B show the phase sensitive reconstruction and the direction of the flow (see FIG. 1) can be determined from FIG. 3B. The phase sensitive reconstructed image is shown in FIG. 4A with the bright signal showing the signal intensity towards the phantom and the dark signal showing the signal away from the phantom. FIG. 4B shows a color depiction in which the arterial signal (red) can be differentiated from venous signal (blue).

Figure 5C:
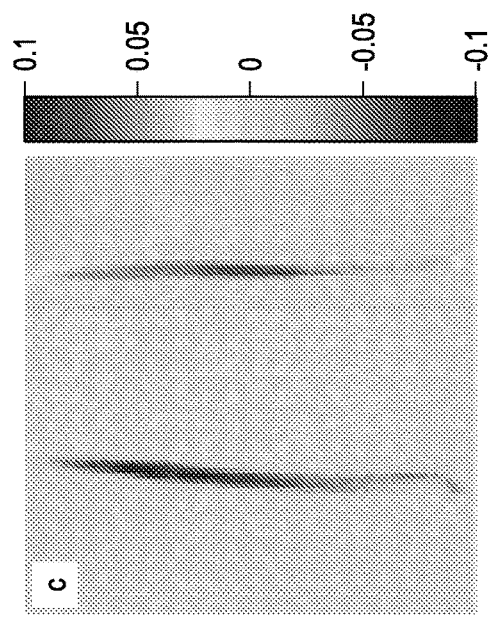
FIGS. 5A to 5C show flow phantom images.

The following is one non-limiting example of an implementation of the present invention. Briefly, a VSP module was implemented in a two dimensional (2D) balanced steady state free precession (bSSFP) acquisition. The skilled artisan will understand that other data acquisition methods can be used to implement the present invention, including but not limited to at least one of: balanced steady state free precession (bSSFP), fast or turbo spin echo (FSE/TSE), or gradient echo. To minimize the sensitivity to $B_0$ and $B_1$ inhomogeneities, an adiabatic pulse (BIR-4 with flip angle (FA) 90°) based VSP was used. All studies were performed on a 3 T Ingenia scanner (Philips Healthcare, The Netherlands). The method was first validated in a flow phantom consisting of tubes with flow in opposite directions submerged in a static water bath (FIG. 5A). The imaging parameters were: TR/TE=3.1/1.56 ms; matrix size=220×216; voxel size=1.1× 1.1×4 mm³; centric phase encoding. The flow was set to 4 cm/s as measured by phase contrast and the corresponding $v_{enc}$ was set to 15 cm/s. An additional image without VSP gradients and BIR-4 FA 0° was acquired to estimate the phase for phase sensitive reconstruction (5). Subsequently, the method was tested on the lower legs of 2 normal volunteers with IRB approval and written informed consent. The acquisition was cardiac triggered to peak systole with the following parameters: coronal orientation; TR/TE=3.0/ 1.5 ms; FOV=334x 167 mm²; resolution=1.1×1.1 mm²; 10 mm slice thickness; centric phase encoding and a $v_{enc}$ of 15 cm/s.

Figure 5B:
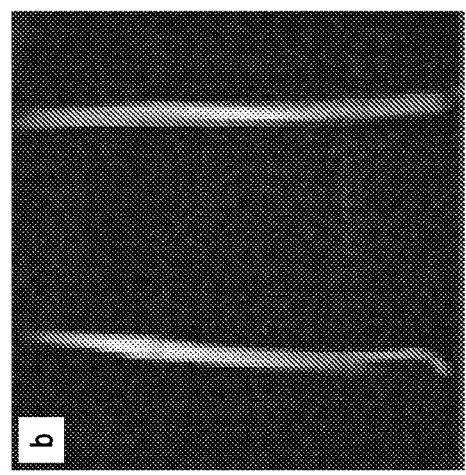
Figure 5A:
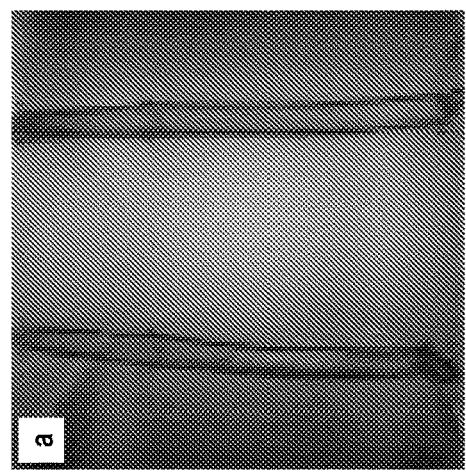
Figure 6A:
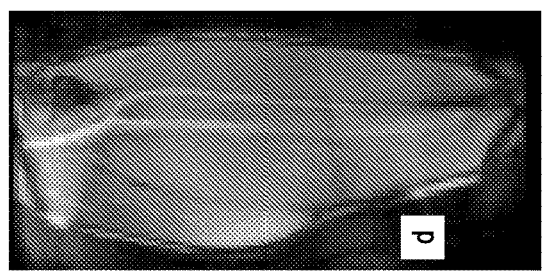
FIGS. 6A to 6D show the results from a normal volunteer study. Phase-sensitive reconstructed images acquired with VSP using.
Figure 6B:
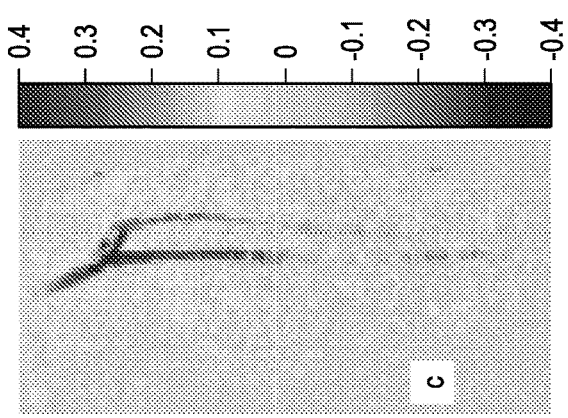
Figure 6C:
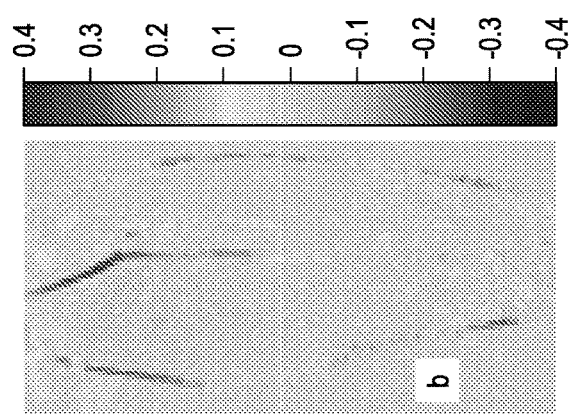
Figure 6D:
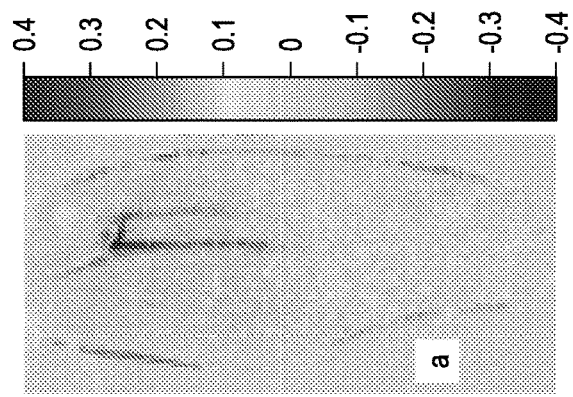

FIG. 5B shows the magnitude image of the flow phantom using the proposed VSP, with essentially no background signal. Using the phase information from the reference image (FIG. 5A), phase sensitive reconstruction allowed estimation of the flow direction (FIG. 5C). Similarly, the direction of the popliteal arteries was also estimated using the phase sensitive reconstruction in the normal volunteer (FIG. 6A). When the VSP was applied with gradients in the opposite direction, the phase sensitive reconstruction appropriately determined the direction of the arterial flow (FIG. 6B). A subtraction between the two images provided the angiogram with good background signal suppression (FIG. 6C). FIG. 6D is the reference image used for phase sensitive reconstruction.

Figure 7A:
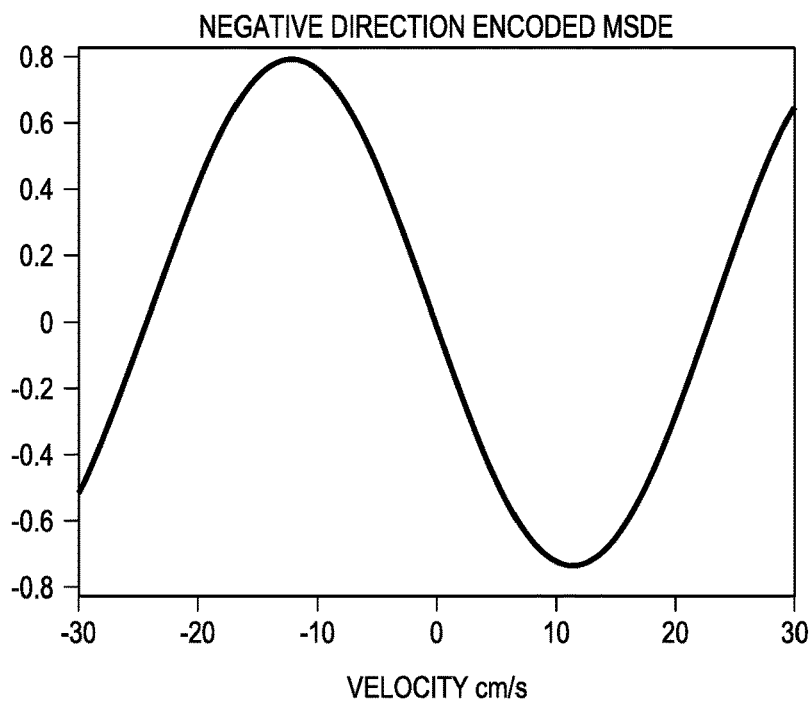
FIG. 7A shows a graph of positive direction encoded MSDE, and the resulting graph.
Figure 7B:
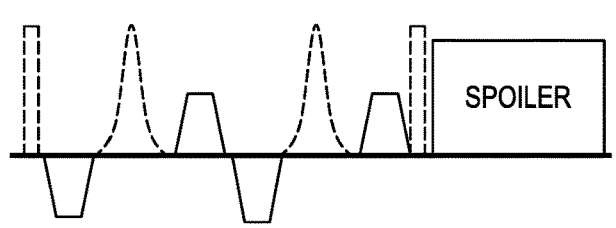
FIG. 7B shows a graph of negative direction encoded MSDE, and the resulting graph.
Figure 7B:
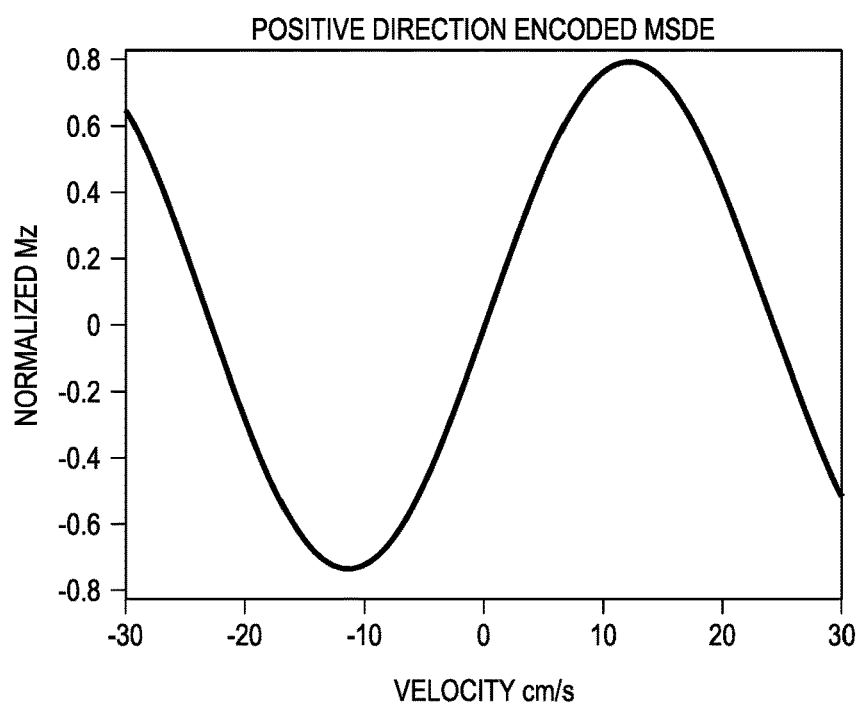

FIG. 7A shows a graph of positive direction encoded MSDE, and the resulting graph. FIG. 7B shows a graph of negative direction encoded MSDE, and the resulting graph. Together, these two graphs show that by switching the gradient direction, the signal intensity is inverted. As such, the subtraction between positive and negative direction encoded images can minimize the background signal due to B0 and B1 inhomogeneities.

Figure 8:
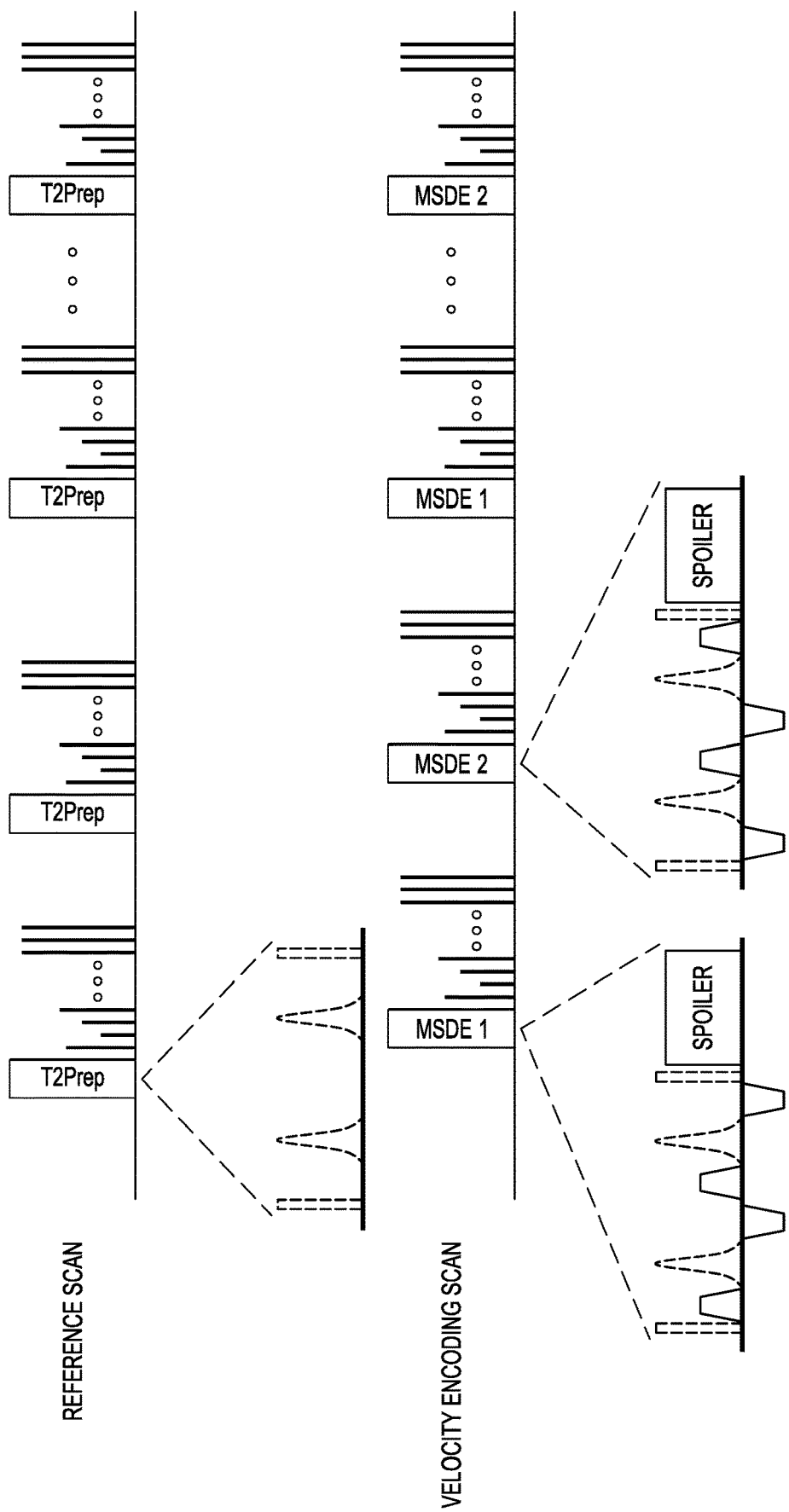
FIG. 8 shows a reference acquisition scan and an interleaved acquisition scan for use with the present invention.

The present invention can also use an interleaved acquisition approach. As shown in FIG. 8, the top data acquisition graph shows the acquisition of a reference scan, using a T2prep method, having two peaks and an interleaved acquisition. In the bottom plan of FIG. 8, the interleaved data acquisition used the MSDE1 and MSDE2 method, as shown in the graph below, the interleaved data acquisition uses both the MSDE methods show in detail in FIGS. 7A and 7B.

Figure 9:
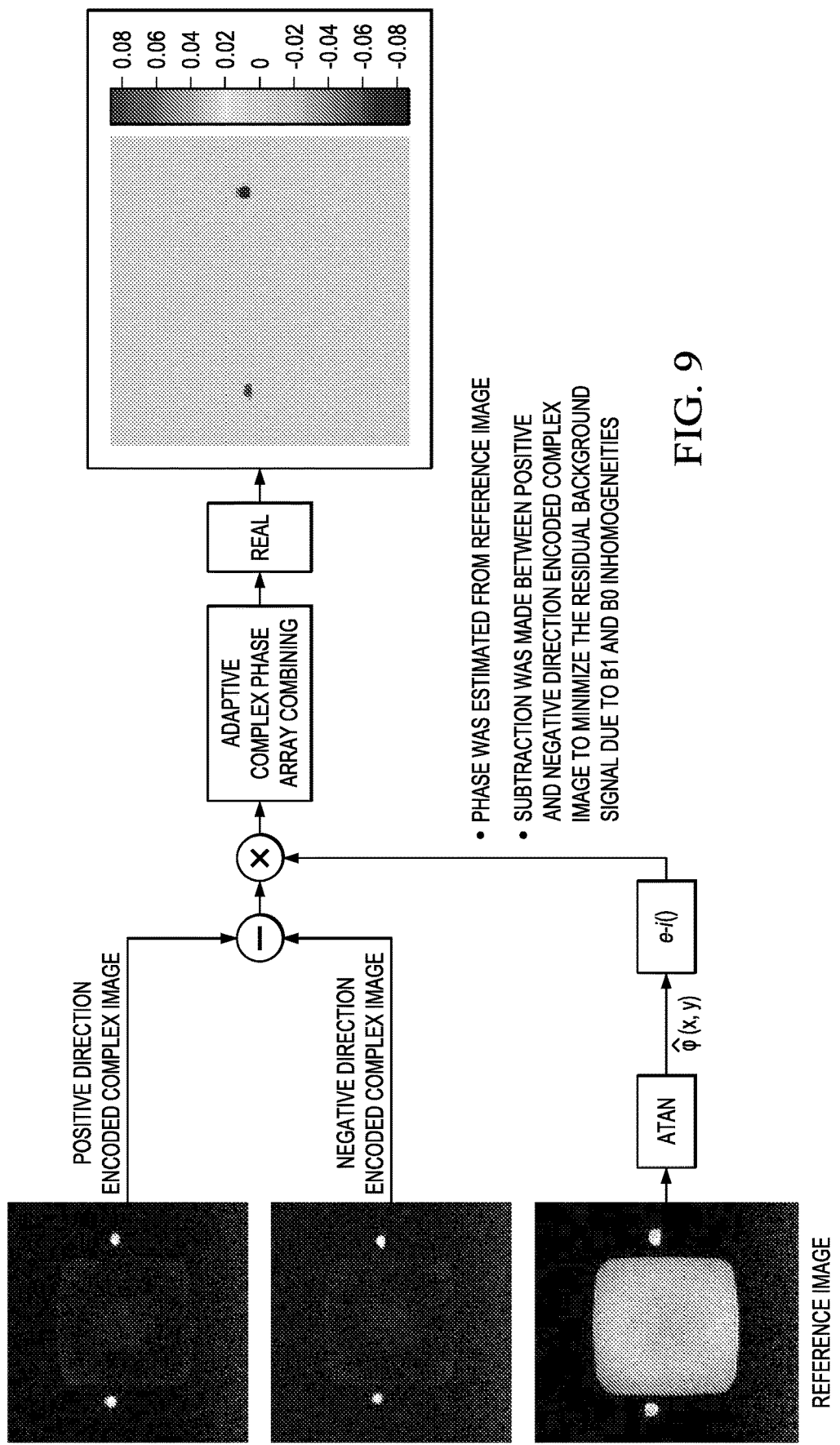
FIG. 9 summarizes the method of phase sensitive reconstruction of the present invention.

FIG. 9 summarizes the method of phase sensitive reconstruction of the present invention. Beginning on the top left, a positive direction encoded complex image is obtained, below that image is the negative direction encoded complex image, and below that image is the reference image. The calculations and combination of these images is next shown as mathematical formulas, to obtain an adaptive complex phase array image by combining the three images. Next, the data acquired is converted into a real image. In this image, the phase was estimated from reference image. In the subtraction step, the subtraction was made between positive and negative direction encoded complex image to minimize the residual background signal due to B1 and B0 inhomogeneities.

Figure 10:
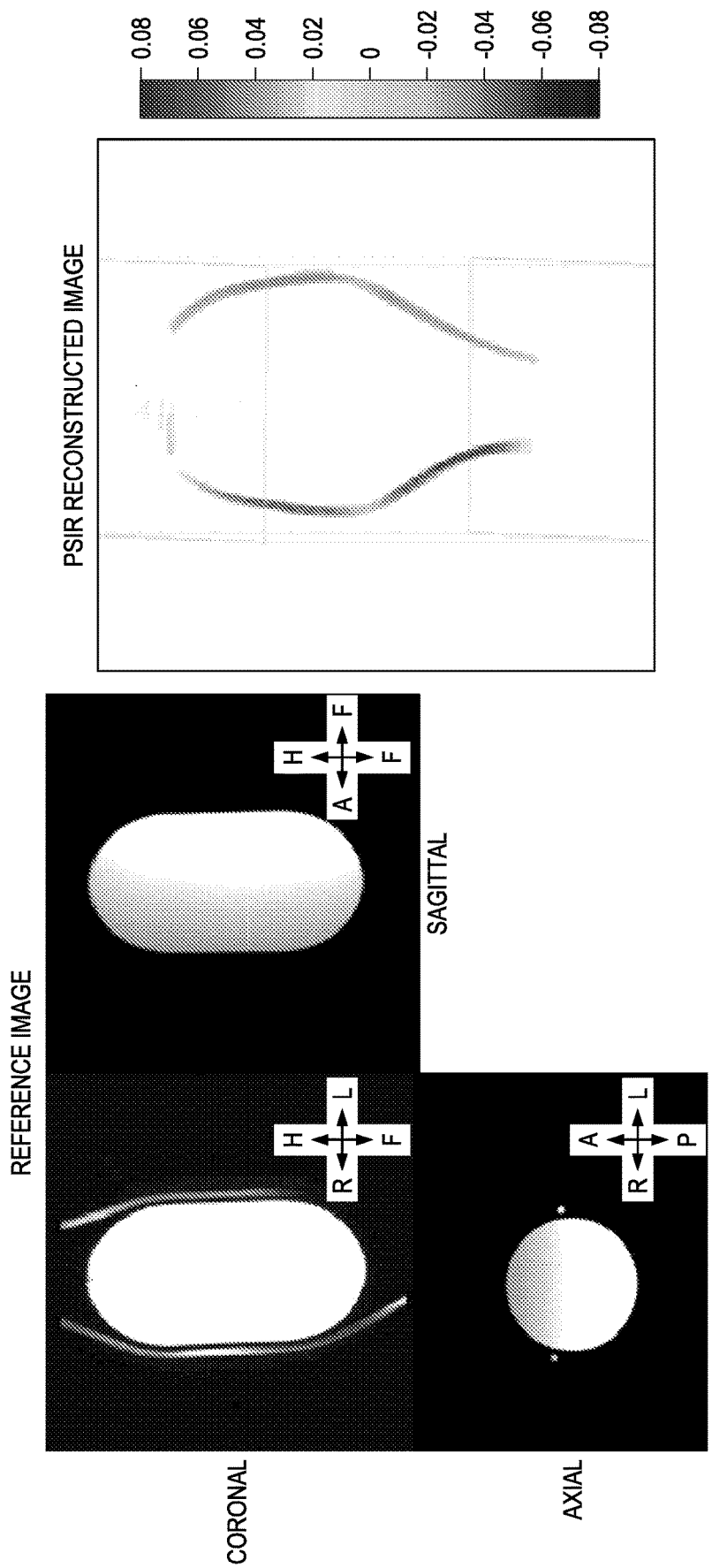
FIG. 10 shows another example of using the present invention with a phantom 3D acquisition showing the reference image from a coronal, axial and sagittal view captured using the present invention, and then the phase-sensitive inversion recovery (PSIR) reconstructed image.

FIG. 10 shows another example of using the present invention with a phantom 3D acquisition showing the reference image from a coronal, axial and sagittal view captured using the present invention, and then the PSIR reconstructed image.

Figure 11:
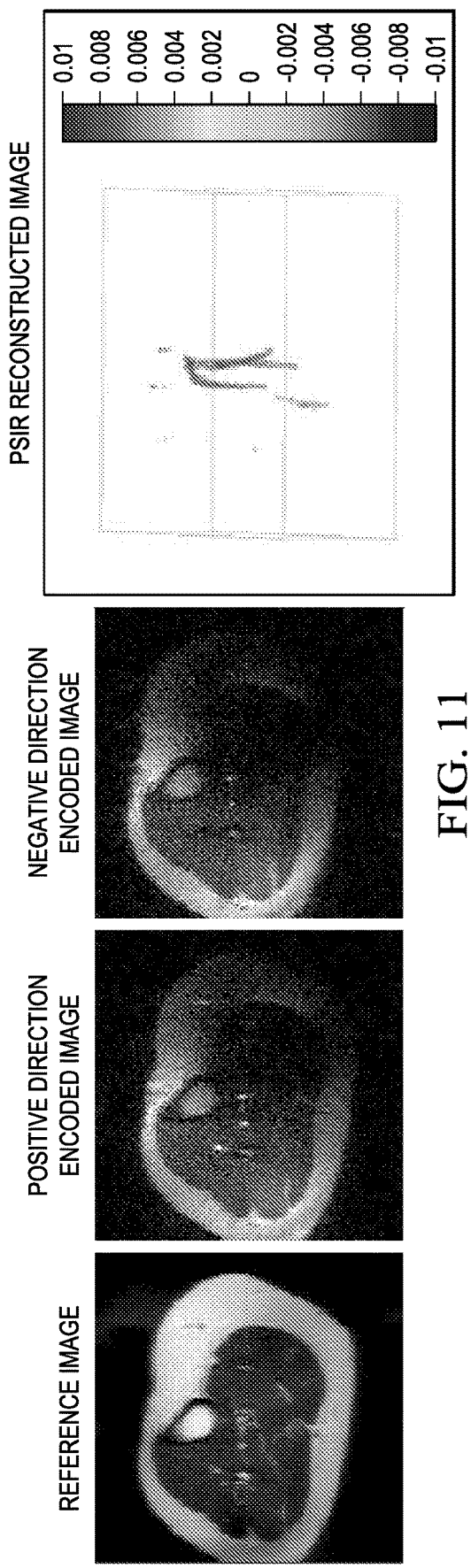
FIG. 11 shows another example of using the present invention of a volunteer with 3D acquisition showing the reference image, the positive direction encoded image, the negative direction encoded image, and the PSIR reconstructed image.

FIG. 11 shows another example of using the present invention of a volunteer with 3D acquisition showing the reference image, the positive direction encoded image, the negative direction encoded image, and the PSIR reconstructed image. Subtraction was made between positive and negative direction encoded image to minimize the residual background signal. The artery of the volunteer is shown in the PSIR reconstructed image.

Thus, the present invention uses phase sensitive acquisition and reconstruction combined with velocity selective preparation allowing the separation of flow depending upon the direction with minimal background signal suppression. The velocity selective preparation of the present invention enables velocity encoding and background suppression simultaneously. While some background signal in the human studies was not completely suppressed, e.g., fat, the subtraction between the two preparation images minimized the background signal and provided a clear image.

Figure 12:
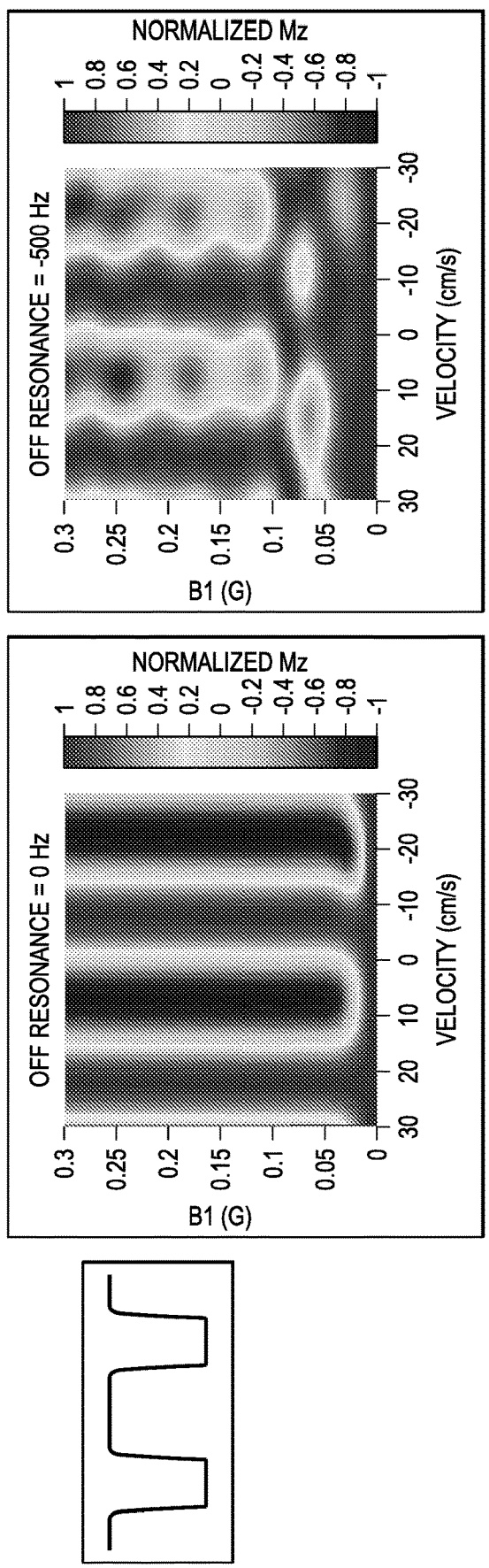
FIG. 12 shows an example of the use of the BIR4 method with the present invention.

Further, the BIR4 method can be used with the present invention. Compared to iMSDE, it was found that BIR4 was insensitive to B0 and B1 inhomogeneity. FIG. 12 shows an example of the use of the BIR4 method with the present invention. The BIR4 acquisition method was as follows: T=16 ms, lambda=15, beta=1.5, and wrf=4.2 KHz.

In another embodiment of the present invention, the background signal, particularly of fat, can be further suppressed with VSP with chemical-shift acquisitions to minimize this signal. Further optimization of the velocity encoding gradients combined with, e.g., 3D bSSFP acquisitions, allows for the separation of arteries and veins with minimal background signal in a single acquisition.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Broome D R. Nephrogenic systemic fibrosis associated with gadolinium based contrast agents: a summary of the medical literature reporting. Eur J Radiol 2008; 66(2): 230-234.
2. Miyazaki M, Lee V S. Nonenhanced MR angiography. Radiology 2008; 248(1):20-43.
3. Fan Z, Sheehan J, Bi X, Liu X, Carr J, Li D. 3D noncontrast MR angiography of the distal lower extremities using flow-sensitive dephasing (FSD)-prepared balanced SSFP. Magn Reson Med 2009; 62(6): 1523-1532.
4. Korosec F R, Grist T M, Polzin J A, Weber D M, Mistretta C A. MR angiography using velocity selective preparation pulses and segmented gradient-echo acquisition. Magn Reson Med 1993; 30(6):704-714.
5. Kellman P, Arai A E, McVeigh E R, Aletras A H. Phase-sensitive inversion recovery for detecting myocardial infarction using gadolinium-delayed hyperenhancement. Magn Reson Med 2002; 47(2):372-383.

What is claimed is:

1. A computerized method of detecting fluid flow in a vessel, the method comprising:
    obtaining at least one non-contrast enhanced magnetic resonance image from a magnetic resonance imager;
    performing a phase sensitive reconstruction of the at least one non-contrast enhanced magnetic resonance image using a processor;
    combining the phase sensitive reconstruction with a velocity selective preparation of the non-contrast enhanced magnetic resonance image, to determine using the processor, in a single acquisition, at least one of: a flow direction of a fluid in the vessel, a reduction or elimination of a background signal, body fat, water/fat separation, or differentiation of a fast moving flow signal from a slow moving flow signal in the opposite direction with suppression of the background signal;
    obtaining an additional image using $90°_{-x}$-$180°_{-y}$-$90°_{-x}$ without a velocity selective preparation gradient, wherein the additional image is used to determine a phase for the phase sensitive reconstruction; and
    storing or displaying at least one of flow direction or flow strength of the fluid flow in the vessel obtained from the single acquisition.

2. The method of claim 1, further comprising the step of velocity selective preparation using a magnetization preparation from one or more $90°_{-x}$-$180°_{-y}$-$90°_{-x}$ radio frequency (RF) pulse trains.

3. The method of claim 1, further comprising the step of velocity selective preparation using a magnetization preparation using a $90°_{-x}$-$180°_{-y}$-$90°_{-x}$ radio frequency (RF) pulse train with one or more velocity encoding gradients applied between one or more RF pulses of the RF pulse train.

4. The method of claim 1, further comprising the step of velocity selective preparation using a process implemented in a 2D balanced steady state free precession (bSSFP) acquisition.

5. The method of claim 1, further comprising the step of using a B1-insensitive rotation (BIR-4) pulse with flip angle (FA) 90° with velocity selective gradients to acquire a velocity sensitive image with high efficiency and another image using BIR-4 pulse with FA 0° and without velocity selective gradients to determine phase for the phase sensitive reconstruction.

6. The method of claim 1, further comprising the step of obtaining an image of a blood vessel of an animal or a human.

7. The method of claim 1, further comprising the step of detecting the moving flow signal in one direction from an arterial flow and the moving flow signal from a venous flow in the opposite direction.

8. The method of claim 1, further comprising the step of acquiring a reference image using $90°_{-x}$-$180°_{-y}$-$90°_{-x}$, or BIR-4 with flip angle (FA) 0°, and a magnitude image is acquired with velocity selective preparation, and using the reference image and the magnitude image to obtain a phase sensitive image that shows flow direction.

9. The method of claim 1, wherein the step of obtaining the image is defined further as comprising a data acquisition method selected from at least one of: balanced steady state free precession (bSSFP), fast or turbo spin echo (FSE/TSE), or gradient echo.

10. The method of claim 1, wherein the step of obtaining the bSSFP image is defined further as using at least one imaging parameter selected from: TR/TE=3.1/1.56 ms, matrix size=220×216, voxel size=1.1×1.1×4 mm$^3$, or centric phase encoding.

11. A computerized method of performing an angiography that separates arterial from venous flow comprising:
   providing a magnetic resonance imager;
   obtaining at least one non-contrast enhanced magnetic resonance image of a blood vessel with the magnetic resonance imager;
   performing a phase sensitive reconstruction of the at least one non-contrast enhanced magnetic resonance image of the blood vessel using a processor;
   combining the phase sensitive reconstruction with a velocity selective preparation of the non-contrast enhanced magnetic resonance image of the blood vessel, to determine using the processor, in a single acquisition, at least one of: a flow direction of blood in the blood vessel, a reduction or elimination of a background signal caused by venous flow, body fat, water/fat separation, or differentiation of a fast moving arterial blood flow signal from a slow moving venous blood flow signal in the opposite direction with suppression of the background signal;
   obtaining an additional image using $90°_{-x}$-$180°_{-y}$-$90°_{-x}$, without a velocity selective preparation gradient, wherein the additional image is used to determine a phase for the phase sensitive reconstruction; and
   storing or displaying at least one of flow direction or flow strength of the fluid flow in the vessel obtained from the single acquisition.

12. The method of claim 11, further comprising the step of velocity selective preparation using a magnetization preparation from one or more $90°_x$-$180°_y$-$90°_y$ radio frequency (RF) pulse trains.

13. The method of claim 11, further comprising the step of velocity selective preparation using a magnetization preparation using a $90°_{-x}$-$180°_{-y}$-$90°_{-x}$ radio frequency (RF) pulse train with one or more velocity encoding gradients applied between one or more RF pulses of the RF pulse train.

14. The method of claim 11, further comprising the step of velocity selective preparation using a process implemented in a 2D balanced steady state free precession (bSSFP) acquisition.

15. The method of claim 11, further comprising the step of using a B1-insensitive rotation (BIR-4) pulse with flip angle (FA) 90° with velocity selective gradients to acquire a velocity sensitive image with high efficiency and another image using a BIR-4 pulse with FA 0° and without velocity selective gradients to determine phase for the phase sensitive reconstruction.

16. The method of claim 11, further comprising the step of obtaining an image of a blood vessel of an animal or a human.

17. The method of claim 11, further comprising the step of detecting the fast moving flow signal in a first direction from an arterial flow and the slow moving flow signal from a venous flow in the opposite direction.

18. The method of claim 11, further comprising the step of acquiring a reference image using $90°_x$-$180°_y$-$90°$, or BIR-4 with flip angle (FA) 0°, and a magnitude image is acquired with velocity selective preparation, and using the reference image and the magnitude image to obtain a phase sensitive image that shows flow direction.

19. The method of claim 11, wherein the method of obtaining the image is defined further as comprising a data acquisition method selected from at least one of: balanced steady state free precession (bSSFP), fast or turbo spin echo (FSE/TSE), or gradient echo.

20. The method of claim 11, wherein the step of obtaining a bSSFP image is defined further as using at least one imaging parameter selected from: TR/TE=3.1/1.56 ms, matrix size=220x216, voxel size=1.1×1.1×4 mm$^{3'}$ or centric phase encoding.

21. A magnetic resonance imaging apparatus comprising:
   a non-transitory computer readable medium and a computer in communication with the magnetic resonance imager that determines at least one of flow direction or flow strength of a fluid flow in a blood vessel, comprising instructions stored thereon, that when executed by the computer having a communications interface, one or more databases and one or more processors communicably coupled to the interface and one or more databases, wherein the one or more processors perform the steps comprising:
      obtaining at least one non-contrast enhanced magnetic resonance image with the magnetic resonance imager;
      performing a phase sensitive reconstruction of the at least one non-contrast enhanced magnetic resonance image using a processor;
      combining the phase sensitive reconstruction with a velocity selective preparation of the of the non-contrast enhanced magnetic resonance image with the processor to determine at least one of a flow direction of a fluid in the vessel, a reduction or elimination of a background signal, or differentiation of a fast moving arterial blood flow signal from a slow moving venous blood flow signal in an opposite direction with suppression of the background signal in a single acquisition;
      obtaining an additional image using $90°_{-x}$-$180°_{-y}$-$90°_{-x}$ without a velocity selective preparation gradient, wherein the additional image is used to determine a phase for the phase sensitive reconstruction; and
      storing or displaying at least one of flow direction or flow strength of the fluid flow in the vessel obtained from the single acquisition.

22. The apparatus of claim 21, further comprising the step of velocity selective preparation using a magnetization preparation using a $90°_{-x}$-$180°_{-y}$-$90°_{-x}$ radio frequency (RF) pulse train with one or more velocity encoding gradients applied between one or more RF pulses of the RF pulse train.

23. A non-transitory computer readable medium for determining at least one of flow direction or flow strength of a fluid flow in a blood vessel, comprising instructions stored thereon, that when executed by a computer having a communications interface, one or more databases and one or more processors communicably coupled to the interface and one or more databases, perform the steps comprising:
   providing a magnetic resonance imager;
   obtaining at least one non-contrast enhanced magnetic resonance image with the magnetic resonance imager;
   performing a phase sensitive reconstruction of the at least one non-contrast enhanced magnetic resonance image using a processor;
   combining the phase sensitive reconstruction with a velocity selective preparation of the non-contrast enhanced magnetic resonance image with the processor to determine at least one of a flow direction of a fluid in the vessel, a reduction or elimination of a background signal, or differentiation of a fast moving arterial blood flow signal from a slow moving venous blood flow signal in an opposite direction with suppression of the background signal in a single acquisition;

obtaining an additional image using $90°_{-x}$-$180°_{-y}$-$90°_{-x}$ without a velocity selective preparation gradient, wherein the additional image is used to determine a phase for the phase sensitive reconstruction; and storing on the computer or in the one or more databases or displaying on the communications interface, at least one of the flow direction or the flow strength of the fluid flow in the blood vessel obtained from the single acquisition.

\* \* \* \* \*